United States Patent [19]
Dean et al.

[11] Patent Number: 5,833,942
[45] Date of Patent: *Nov. 10, 1998

[54] TECHNETIUM-99M LABELED SOMATOSTATIN-DERIVED PEPTIDES FOR IMAGING AND THERAPEUTIC USES

[75] Inventors: Richard T. Dean; John Lister-James, both of Bedford, N.H.

[73] Assignee: Diatide, Inc., Londonderry, N.H.

[*] Notice: The term of this patent shall not extend beyond the expiration date of Pat. No. 5,716,596.

[21] Appl. No.: 470,932

[22] Filed: Jun. 6, 1995

Related U.S. Application Data

[62] Division of Ser. No. 902,935, Jun. 23, 1992, Pat. No. 5,716,596.

[51] Int. Cl.$^6$ .......................... A61K 51/08; A61K 38/31; C07K 5/00
[52] U.S. Cl. ...................... 424/1.41; 424/1.69; 424/1.53; 530/311; 514/806; 930/160
[58] Field of Search .................... 424/1.69, 1.65, 424/1.41, 1.53, 1.57; 514/806; 530/311, 300, 336; 930/160

[56] References Cited

U.S. PATENT DOCUMENTS

| | | | |
|---|---|---|---|
| 4,235,886 | 11/1980 | Freidinger | 424/117 |
| 4,244,947 | 1/1981 | Abraham et al. | 424/177 |
| 4,444,690 | 4/1984 | Fritzberg | 260/429 |
| 4,472,509 | 9/1984 | Gansow et al. | 436/548 |
| 4,485,101 | 11/1984 | Coy et al. | 424/177 |
| 4,611,054 | 9/1986 | Freidinger | 530/311 |
| 4,612,366 | 9/1986 | Nutt | 530/311 |
| 4,650,787 | 3/1987 | Schally et al. | 514/11 |
| 4,684,620 | 8/1987 | Hruby et al. | 514/11 |
| 4,853,371 | 8/1989 | Coy et al. | 514/12 |
| 4,871,717 | 10/1989 | Coy et al. | 514/11 |
| 4,904,642 | 2/1990 | Coy et al. | 514/11 |
| 5,066,716 | 11/1991 | Robey | 525/54.1 |
| 5,095,111 | 3/1992 | Lever et al. | 540/544 |
| 5,196,510 | 3/1993 | Rodwell | 424/1.1 X |
| 5,225,180 | 7/1993 | Dean et al. | 424/1.1 |
| 5,443,806 | 8/1995 | Zamora et al. | 424/1.69 |
| 5,508,020 | 4/1996 | Dean et al. | 424/1.69 |

FOREIGN PATENT DOCUMENTS

| | | | |
|---|---|---|---|
| 83111747 | 11/1983 | European Pat. Off. | C07C 103/52 |
| 85810617 | 12/1985 | European Pat. Off. | C07K 7/100 |
| 87300426 | 1/1987 | European Pat. Off. | C07B 59/00 |
| 90302760 | 3/1990 | European Pat. Off. | C07K 7/06 |
| 0453082 | 10/1991 | European Pat. Off. | A61K 39/44 |
| 2320109 | 3/1977 | France . | |
| 2336943 | 7/1977 | France | A61K 37/24 |
| 89 27255 | 1/1989 | United Kingdom | C07K 7/26 |
| WO8807382 | 4/1988 | WIPO | A61K 49/02 |
| WO8910759 | 11/1989 | WIPO . | |
| 9006949 | 6/1990 | WIPO | A61K 43/00 |
| WO9006949 | 6/1990 | WIPO | A61K 43/00 |
| WO9101144 | 7/1990 | WIPO | A61K 43/00 |

OTHER PUBLICATIONS

Albert et al., "A Somatostatin Analogue to Image SS–Receptor–Positive Tumours: [$^{111}$In–DTPA–Dphe]$1^1$–Octreotide (SDZ 215–811)", *Abstract LM10, 12$^{th}$ American Peptide Symposium:* 1991.

Arano et al., "A Novel Bifunctional Metabolisable Linker for the Conjugation of antibodies with Radionucleotides", Bioconj. Chem. vol. 2, No. 2, 1991, pp. 71–76.

Bakker et al., "In Vivo Use of a Radioiodinated Somatostatin Analogue: Dynamics, Metabolism, and Binding to Somatostatin Receptor–Positive Tumors in Man," *J. Nucl. Med.* 32:1184–1189 (1991).

Bakker et al., "Receptor Scintigraphy with a Radioiodinated Somatostatin Analogue: Radiolabeling, Purification, Biologic Acitivity, and In Vivo Applications in Animals," *J. Nucl. Med.* 31:1501–1509 (1990).

Bean et al., "Identification of a thioether byproduct in the synthesis of a cyclic disulfide peptide by tandem mass spectrometry," *Peptides; Chemistry, Structure and Biology,* ESCOM, Leiden 1990, pp. 443–445, Rivier et al.

Bryson, "Protecting Groups in the Preparation of Thiolate Complexes of Technetium," *Inorganic Chemistry* vol. 29, No. 16, Aug. 8, 1990, pp. 2948–2951.

Byrne & Tolman, "Technetium–99m Bifunctional Chelating Agent—Thiolactone for Coupling to Biomolecules, $N_2S_2$ Ligand for Chalation to Technetium," *J. Nucl. Med.* 24:126 (1983).

Cox et al., "Technetium Labeled Somatostatin; A Potential Agent for In Vivo Tumour Localization," *Abstract, 7$^{th}$ International Symposium on Radiopharmacology,* p. 16 (1991).

Khaw et al., "Technetium –99m Labeling of Antibodies to Cardiac Myosin Fab and to Human Fibrinogen," *J. Nucl. Med.* 23:1011–1019 (1982).

Kwekkeboom et al., "[In–111–DTPA–D–Phe]–Octreotide Scintigraphy in Neuro–endocrine Tumors," *J. Nucl. Med.* 32:981 Abstract ™305 (1991).

Lamberts, "Receptors on Tumors Studied with Radionuclide Scintigraphy", *J. Nucl. Med.* 32:1189–1191 (1991).

(List continued on next page.)

*Primary Examiner*—Gary E. Hollinden
*Assistant Examiner*—Michael G. Hartley
*Attorney, Agent, or Firm*—Patricia A. McDaniels; Kevin E. Noonan

[57] ABSTRACT

This invention relates to therapeutic reagents and peptides, radiodiagnostic reagents and peptides, and methods for producing labeled radiodiagnostic agents. Specifically, the invention relates to peptide derivatives and analogs of somatostatin, and embodiments of such peptides labeled with technetium-99m (Tc-99m), as well as methods and kits for making, radiolabeling and using such peptides to image sites in a mammalian body. The invention also relates to peptide derivatives and analogues of somatostatin labeled with rhemium-186 ($^{186}$Re) and rhenium-188 ($^{188}$Re), and methods and kits for making, radiolabeling and using such peptides therapeutically in a mammalian body.

11 Claims, No Drawings

OTHER PUBLICATIONS

Li et al., "A New Bifunctional Chelating Agent Alpha, Epsilon–N,N'–bis (L–Cyteinyl)–L –Lysine For Radiolabeleing of Monoclonal antibodies with TX–99M," Chemical Abstracts, Oct. 14, 1991, vol. 115, No. 15, abstract No. 159733, p. 1001, col. 2.

Rhodes, "Considerations in the Radiolabeling of Albumin," *Sem. Nucl. Med.* 4:281–293 (1974).

Gero et al., "Synthesis and Biological Activity of a Cyclic Pseudo–Hexapeptide Analog of Somatostatin" Biochemical and Biophysical Research Communications, vol. 120, No. 3, pp. 840–845, May 1994.

TECHNETIUM-99M LABELED SOMATOSTATIN-DERIVED PEPTIDES FOR IMAGING AND THERAPEUTIC USES

This application is a divisional of U.S. application Ser. No. 07/902,935, filed Jun. 23, 1992 and now U.S. Pat. No. 5,716,596, issued Feb. 10, 1998.

BACKGROUND OF THE INVENTION

1. Field of the Invention

This invention relates to therapeutic reagents and peptides, radiodiagnostic reagents and peptides, and methods for producing labeled radiodiagnostic and radiotherapeutic agents. Specifically, the invention relates to peptide derivatives and analogues of somatostatin, and embodiments of such peptides labeled with technetium-99m (Tc-99m), as well as methods and kits for making, radiolabeling and using such peptides to image sites in a mammalian body. The invention also relates to peptide derivatives and analogues of somatostatin labeled with rhenium-186 ($^{186}$Re) and rhenium-188 ($^{188}$Re), and methods and kits for making, radiolabeling and using such peptides therapeutically in a mammalian body.

2. Description of the Prior Art

Somatostatin is a tetradecapeptide that is endogenously produced by the hypothalamus and pancreas in humans and other mammals. The peptide has the formula:

Formula I

[Single letter abbreviations for amino acids can be found in G. Zubay, *Biochemistry* (2d ed.), 1988, (MacMillan Publishing: New York), p.33]. This peptide exerts a wide variety of biological effects in vivo. It is known to act physiologically on the central nervous system, the hypothalamus, the pancreas, and the gastrointestinal tract.

Somatostatin inhibits the release of insulin and glucagon from the pancreas, inhibits growth hormone release from the hypothalamus, and reduces gastric secretions. Thus, somatostatin has clinical and therapeutic applications for the alleviation of a number of ailments and diseases, both in humans and other animals. Native somatostatin is of limited utility, however, due to its short half-life in vivo, where it is rapidly degraded by peptidases. For this reason, somatostatin analogues having improved in vivo stability have been developed in the prior art.

Freidinger, U.S. Pat. No. 4,235,886 disclose cyclic hexapeptide somatostatin analogues useful in the treatment of a number of diseases in humans.

Freidinger, U.S. Pat. No. 4,611,054 disclose cyclic hexapeptide somatostatin analogues useful in the treatment of a number of diseases in humans.

Nutt, U.S. Pat. No. 4,612,366 disclose cyclic hexapeptide somatostatin analogues useful in the treatment of a number of diseases in humans.

Coy et al., U.S. Pat. No. 4,853,371 disclose synthetic octapeptide somatostatin analogues.

Coy and Murphy, U.S. Pat. No. 4,871,717 disclose synthetic heptapeptide somatostatin analogues.

Coy and Murphy, U.S. Pat. No. 4,485,101 disclose synthetic dodecapeptide somatostatin analogues.

Coy et al., U.S. Pat. No. 4,904,642 disclose synthetic octapeptide somatostatin analogues.

Brady, European Patent Application No. 83111747.8 discloses dicyclic hexapeptide somatostatin analogues useful in the treatment of a number of human diseases.

Bauer et al., European Patent Application No. 85810617.2 disclose somatostatin derivatives useful in the treatment of a number of human diseases.

Eck and Moreau, European Patent Application No. 90302760.5 disclose therapeutic octapeptide somatostatin analogues.

Somatostatin exerts it effects by binding to specific receptors expressed at the cell surface of cells comprising the central nervous system, the hypothalamus, the pancreas, and the gastrointestinal tract. These high-affinity somatostatin binding sites have been found to be abundantly expressed at the cell surface of most endocrine-active tumors arising from these tissues. Expression of high-affinity binding sites for somatostatin is a marker for these tumor cells, and specific binding with somatostatin can be exploited to locate and identify tumor cells in vivo.

Methods for radiolabeling somatostatin analogues that have been modified so as to contain a tyrosine amino acid (Tyr or Y) are known in the prior art.

Albert et al., UK Patent Application 8927255.3 disclose radioimaging using somatostatin derivatives such as octreotide labeled with $^{123}$I.

Bakker et al., J. Nucl. Med. 31: 1501–1509 (1990) describe radioactive iodination of a somatostatin analog and its usefulness in detecting tumors in vivo.

Bakker et al., J. Nucl. Med. 32: 1184–1189 (1991) teach the usefulness of radiolabeled somatostatin for radioimaging in vivo.

Alternatively, methods for radiolabeling somatostatin by covalently modifying the peptide to contain a radionuclide-chelating group have been disclosed in the prior art.

Albert et al., UK Patent Application 8927255.3 disclose radioimaging using somatostatin derivatives such as octreotide labeled with $^{111}$In via a chelating group bound to the amino-terminus.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Kwekkeboom et al., J. Nucl. Med. 32: 981 (1991) Abstract #305 relates to radiolabeling somatostatin analogues with $^{111}$In.

Albert et al., Abstract LM10, 12th American Peptide Symposium: 1991 describe uses for $^{111}$In-labeled diethylene-triaminopentaacetic acid-derivatized somatostatin analogues.

These methods can be readily adapted to enable detection of tumor cells in vivo based on their expression of high affinity binding sites for somatostatin by radioimaging. Radionuclides which emit high energy gamma radiation can be readily detected by scintigraphy after injection into a human or an animal. A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. The sensitivity of imaging methods using radioactively-labeled peptides is much higher than other techniques known in the art, since the specific binding of the radioactive peptide concentrates the radioactive signal over the cells of interest, for example, tumor cells. This is particularly important for endocrine-active gastrointestinal tumors, which are usually small, slow-growing and difficult to detect by conventional methods. Labeling with technetium-99m (Tc-99m) is advantageous because the nuclear and radioactive properties of this isotope make it an ideal scintigraphic imaging agent. Tc-99m has a single photon energy of 140 keV and a radioactive half-life of about 6 hours, and is readily available from a $^{99}$Mo-$^{99m}$Tc generator. Other radionuclides have effective half-lives which are much longer (for example, $^{111}$In, which has a half-life of 60–70 h) or are toxic (for example, $^{125}$I). Although Tc-99m is an ideal radiolabeling reagent, it has not been widely used in the art prior to the present invention [see, for example, Lamberts, J. Nucl. Med. 32: 1189–1191 (1991)].

Radiolabeled somatostatin analogues can also be used therapeutically. For these applications, the rhenium isotopes $^{186}$Re and $^{188}$Re are particularly advantageous.

The use of chelating agents for radiolabeling polypeptides, and methods for labeling peptides and polypeptides with Tc-99m are known in the prior art and are disclosed in copending U.S. patent applications Ser. Nos. 07/653,012, now abandoned, which has been allowed as U.S. Ser. No. 08/480,551; 07/807,062, now U.S. Pat. No. 5,443,815; 07/851,074, now abandoned, which issued as U.S. Pat. No. 5,711,931; 07/871,282, which issued as U.S. Pat. No. 5,720,934; and 07/886,752, now abandoned, which has been allowed as U.S. Ser. No. 08/273,274 which are hereby incorporated by reference.

Fritzberg, U.S. Pat. No. 4,444,690 describes a series of technetium-chelating agents based on 2,3-bis(mercaptoacetamido) propanoate.

Gansow et al., U.S. Pat. No. 4,472,509 teach methods of manufacturing and purifying Tc-99m chelate-conjugated monoclonal antibodies.

Reno and Bottino, European Patent Application 87300426.1 disclose radiolabeling antibodies with Tc-99m.

Pak et al., European Patent Application No. WO 88/07382 disclose a method for labeling antibodies with Tc-99m.

Rhodes, Sem. Nucl. Med. 4: 281–293 (1974) teach the labeling of human serum albumin with technetium-99m.

Khaw et al., J. Nucl. Med. 23: 1011–1019 (1982) disclose methods for labeling biologically active macromolecules with Tc-99m.

Byrne and Tolman, supra, disclose a bifunctional thiolactone chelating agent for coupling Tc-99m to biological molecules.

Cox et al., Abstract, 7th International Symposium on Radiopharmacology, p. 16, 1991, disclose the use of, Tc-99m-, $^{131}$I- and $^{111}$In-labeled somatostatin analogues in radiolocalization of endocrine tumors in vivo by scintigraphy.

Methods for directly labeling somatostatin, derivatives of somatostatin, analogues of somatostatin or peptides that bind to the somatostatin receptor and contain at least 2 cysteine residues that form a disulfide or wherein the disulfide is reduced to the sulfhydryl form, are disclosed in co-pending U.S. patent application Ser. No. 07/807,062, which is hereby incorporated by reference.

There remains a need for synthetic (to make routine manufacture practicable and to ease regulatory acceptance) somatostatin analogues having increased in vivo stability, to be used therapeutically and as scintigraphic agents when radiolabeled with Tc-99m for use in imaging tumors in vivo. Small synthetic somatostatin analogues are provided by this invention that specifically fulfill this need.

SUMMARY OF THE INVENTION

The present invention provides somatostatin analogues for therapeutic and scintigraphic imaging applications that are peptide reagents. Specifically, the invention provides peptide reagents for preparing scintigraphic imaging agents that are technetium-99m (Tc-99m) labeled. The scintigraphic imaging agents of the invention are comprised of a peptide that is a somatostatin analogue covalently linked to a Tc-99m binding moiety and labeled with Tc-99m. In addition, the invention provides somatostatin analogues and such analogues radiolabeled with $^{186}$Re and $^{188}$Re that are useful therapeutically.

The somatostatin analogues provided by the invention are somatostatin-receptor binding peptides having the following formula:

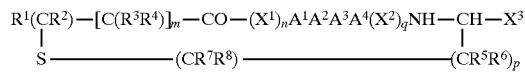

where $R^1$ and $R^2$ are independently H, lower alkyl or substituted alkyl, aryl or substituted aryl;

$R^3$ and $R^4$ are each independently H, lower alkyl or substituted alkyl, aryl or substituted aryl, or either $R^3$ or $R^4$ are $N(R^{10})_2$, where each $R^{10}$ is independently H, lower alkyl or a peptide sequence of no more than 10 amino acids, and m is an integer between 0 and 3;

$X^1$ and $X^2$ are each independently a D- or L- amino acid, and n and q are independently either 0 or 1;

$A^1$ is D- or L-Phe or D- or L-Tyr or substituted derivatives thereof;

$A^2$ is D-or L- Trp or substituted derivatives thereof;

$A^3$ is D- or L-Lys or substituted derivatives thereof;

$A^4$ is Thr, Ser, Val, Phe, Ile or 2-amino-isobutyric acid (Aib), most preferably Thr or Val;

$X^3$ is H, —COOR$^9$, —CH$_2$OH, CH$_2$COOR$^9$, or —CON(R$^9$)$_2$, where each $R^9$ is independently H, lower linear or cyclic alkyl or substituted derivatives thereof, or a peptide having an amino acid sequence of no more than 10 residues;

$R^5$ and $R^6$ are each independently H or lower alkyl and p is either 0, 1 or 2; and $R^7$ and $R^8$ are independently H, lower alkyl or substituted lower alkyl, or either $R^7$ and $R^8$ are —COOH or a derivative thereof.

In a preferred embodiment, $A^1$ is Phe or Tyr, $A^2$ is Trp or most preferably D-Trp, $A^3$ is Lys and $A^4$ is Thr or Val.

In a first aspect of the present invention are provided peptide reagents that are somatostatin analogues as described herein having increased in vivo stability compared with native somatostatin, and that are therapeutically useful in the alleviation of diseases or other ailments in humans or other animals.

The invention also provides pharmaceutical compositions comprising the somatostatin receptor-binding peptides of the invention in a pharmaceutically acceptable carrier.

The invention also provides a method for alleviating somatostatin-related diseases in animals, preferably humans, comprising administering a therapeutically effective amount of the somatostatin analogues of the invention to the animal. In preferred embodiments, the amount of the somatostatin analogue administered is from about 0.1 to about 50 mg/kg body weight/day.

Another aspect of the present invention provides reagents for preparing scintigraphic imaging agents, each reagent comprising a peptide that is a somatostatin analogue and is covalently linked to a Tc-99m binding moiety.

A first aspect of the reagents for preparing scintigraphic imaging agents of the invention are reagents, each comprised of a peptide that is a somatostatin analogue that is covalently linked to a Tc-99m binding moiety having formula:

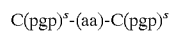

wherein C(pgp)$^s$ is a protected cysteine and (aa) is an amino acid. In a preferred embodiment, the amino acid is glycine.

In a second embodiment, the invention provides peptide reagents capable of being Tc-99m labeled for imaging sites within a mammalian body, each comprising a somatostatin analogue that is covalently linked to a radioisotope complexing group comprising a single thiol moiety having the following structure:

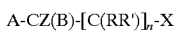

wherein

A is H, HOOC, H$_2$NOC, or —NHOC;

B is SH or NHR";

X is H, methyl, SH or NHR";

Z is H or methyl;

R and R' are independently H or lower alkyl;

R" is H, lower alkyl or —C=O;

n is 0, 1 or 2;

and where B is NHR", X is SH, Z is H and n is 1 or 2; where X is NHR", B is SH, Z is H and n is 1 or 2; where B is H, A is HOOC, H$_2$NOC, or —NHOC, X is SH, Z is H and n is 0 or 1; where Z is methyl, X is methyl, A is HOOC, H$_2$NOC, or —NHOC,, B is SH and n is 0; and wherein the thiol moiety is in the reduced form. In a preferred embodiment, the peptide is comprised between 4 and 30 amino acids.

In another embodiment, the invention provides peptide reagents capable of being labeled with Tc-99m for imaging sites within a mammalian body, each comprising a somatostatin analogue that is covalently linked to a Tc-99m binding moiety of formula:

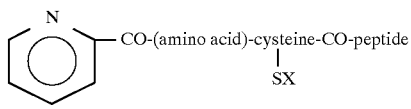

[for purposes of this invention, radiolabel-binding moieties having this structure will be referred to as picolinic acid (Pic)-based moieties] or

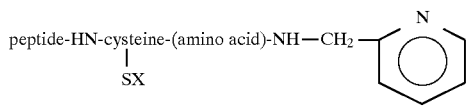

wherein X is H or a protecting group; (amino acid) is any amino acid and the radiolabel-binding moiety is covalently linked to the peptide. For purposes of this invention, radiolabel-binding moieties having this structure will be referred to as picolylamine (Pica)-based moieties. In a preferred embodiment, the amino acid is glycine and X is an acetamidomethyl protecting group. In additional preferred embodiments, the peptide is comprised between 4 and 30 amino acids.

Yet another embodiment of the invention provides peptide reagents capable of being labeled with Tc-99m for imaging sites within a mammalian body, each comprising a somatostatin analogue that is covalently linked to a Tc-99m binding moiety that is a bisamino bisthiol Tc-99m binding moiety. The bisamino bisthiol Tc-99m binding moiety in this embodiment of the invention has a formula selected from the group consisting of:

I.

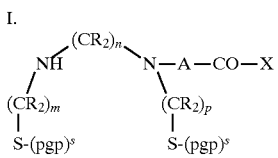

wherein each R can be independently H, CH$_3$ or C$_2$H$_5$;

each (pgp)$^s$ can be independently a thiol protecting group or H;

m, n and p are independently 2 or 3;

A is linear or cyclic lower alkyl, aryl, heterocyclyl, combinations or substituted derivatives thereof; and X is peptide; and

II.

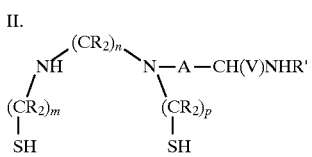

wherein each R is independently H, CH$_3$ or C$_2$H$_5$;

m, n and p are independently 2 or 3;

A is linear or cyclic lower alkyl, aryl, heterocyclyl, combinations or substituted derivatives thereof;

V is H or CO-peptide;

R' is H or peptide;

provided that when V is H, R' is peptide and when R' is H, V is CO-peptide. For purposes of this invention, radiolabel-binding moieties having these structures will be referred to as "BAT" moieties. In a preferred embodiment, the peptide is comprised between 4 and 30 amino acids.

The invention also comprises scintigraphic imaging agents that are complexes of the peptide reagents of the invention with Tc-99m and methods for radiolabeling the peptide reagents of the invention with Tc-99m. Radiolabeled complexes provided by the invention are formed by reacting the peptide reagents of the invention with Tc-99m in the presence of a reducing agent. Preferred reducing agents include but are not limited to dithionite ion, stannous ion and ferrous ion. Complexes of the invention are also formed by labeling the peptide reagents of the invention with Tc-99m by ligand exchange of a prereduced Tc-99m complex as provided herein.

The invention also provides kits for preparing scintigraphic imaging agents that are the peptide reagents of the invention radiolabeled with Tc-99m. Kits for labeling the peptide reagents of the invention with Tc-99m are comprised of a sealed vial containing a predetermined quantity of a peptide reagent of the invention and a sufficient amount of reducing agent to label the peptide with Tc-99m.

This invention provides methods for preparing peptide reagents of the invention by chemical synthesis in vitro. In a preferred embodiment, peptides are synthesized by solid phase peptide synthesis.

This invention provides methods for using scintigraphic imaging agents that are Tc-99m labeled peptide reagents for imaging sites within a mammalian body by obtaining in vivo gamma scintigraphic images. These methods comprise administering an effective diagnostic amount of Tc-99m labeled peptide reagents of the invention and detecting the gamma radiation emitted by the Tc-99m label localized at the site within the mammalian body.

This invention provides reagents for preparing a radiolabled somatostatin receptor-binding agent comprising the somatostatin receptor-binding peptides of the invention covalently linked to a radiolabel-binding moiety. In a preferred embodiment, the reagent is radioactively labeled with Tc-99m. In another preferred embodiment, the reagent is radioactively labeled with $^{186}$Re or $^{188}$Re.

The invention also provides methods for alleviating somatostatin-related diseases in animals, preferably humans, comprising administering a therapeutically effective amount of the radiolabeled somatostatin-binding peptide reagents of the invention to the animal. In preferred embodiments, the reagent is radioactively labeled with $^{186}$Re or $^{188}$Re.

Specific preferred embodiments of the present invention will become evident from the following more detailed description of certain preferred embodiments and the claims.

DETAILED DESCRIPTION OF THE INVENTION

The present invention provides peptide reagents for preparing radiolabeled imaging agents for imaging site within a mammalian body. The peptide reagents of the invention each comprise a somatostatin analogue that is covalently linked to a Tc-99m binding moiety. The invention also provides somatostatin analogues having an increased in vivo stability and that are useful for alleviating diseases or other ailments in humans or other animals.

The invention provides a method for using the somatostatin analogues of the invention to alleviate diseases or other ailments in animals, preferably humans. These diseases and ailments include but are not limited to diabetes and diabetes-related retinopathy, cirrhosis of the liver and hepatitis infection, bleeding ulcers and other gastrointestinal bleeding, pancreatitis, central nervous system disorders, endocrine disorders, Alzheimer's disease, acromegaly and other diseases and disorders related to the production of inappropriate levels of growth hormone in vivo, and cancer, particularly those cancers whose growth is dependent on or influenced by growth hormone production. Dosages of the somatostatin analogues provided by the invention may be the same as those dosages of native somatostatin routinely used for treatment of the above or other diseases, or less of the compounds of the invention may be administered due to their longer in vivo half-life.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides known in the prior art have effective half-lives which are much longer (for example, $^{111}$In, which has a half-life of 67.4 h) or are toxic (for example, $^{125}$I).

Radiotherapeutic embodiments of the invention, on the other hand, are advantageously labeled with $^{186}$Re or $^{188}$Re. Such embodiments are useful in the treatment of somatostatin-related diseases or other ailments in animals, preferably humans, including but not limited to cancer and other diseases characterized by the growth of malignant or benign tumors capable of binding somatostatin or somatostatin analogues via the expression of somatostatin receptors on the cell surface of cells comprising such tumors.

In the Tc-99m binding moieties and peptides covalently linked to such moieties that contain a thiol covalently linked to a thiol protecting groups [(pgp)$^s$] provided by the invention, the thiol-protecting groups may be the same or different and may be but are not limited to:

—CH$_2$-aryl (aryl is phenyl or alkyl or alkyloxy substituted phenyl);

—CH-(aryl)$_2$, (aryl is phenyl or alkyl or alkyloxy substituted phenyl);

—C-(aryl)$_3$, (aryl is phenyl or alkyl or alkyloxy substituted phenyl);

—CH$_2$-(4-methoxyphenyl);

—CH-(4-pyridyl)(phenyl)$_2$;

—C(CH$_3$)$_3$

-9-phenylfluorenyl;

—CH$_2$NHCOR (R is unsubstituted or substituted alkyl or aryl);

—CH$_2$—NHCOOR (R is unsubstituted or substituted alkyl or aryl);

—CONHR (R is unsubstituted or substituted alkyl or aryl);

—CH$_2$—S—CH$_2$-phenyl

Preferred protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Each specific-binding peptide provided by the invention is comprised of a sequence of amino acids. The term amino acid as used in this invention is intended to include all L- and D- amino acids, naturally occurring and otherwise, and substituted derivatives thereof. Specific-binding peptides provided by the invention include but are not limited to peptides having the following sequences:

Specific-binding peptides of the present invention can be chemically synthesized in vitro. Peptides of the present invention can generally advantageously be prepared on an amino acid synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

Radiolabel binding moieties of the invention may be introduced into the target specific peptide during peptide synthesis. For embodiments comprising picolinic acid [(Pic-); e.g., Pic-Gly-Cys(protecting group)-], the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group) ], which may be incorporated at any position in the peptide chain. This sequence is particularly advantageous as it affords an easy mode of incorporation into the target binding peptide.

Similarly, the picolylamine (Pica)-containing radiolabel-binding moiety [-Cys(protecting group)-Gly-Pica] can be prepared during peptide synthesis by including the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

This invention also provides small synthetic peptides that are somatostatin analogues and incorporate bisamine bisthiol (BAT) chelators that may be labeled with Tc-99m.

This invention provides for the incorporation of these chelators into virtually any position in the peptide, via covalent linkage to any appropriate functional group of the peptide, except that the chelating moieties of the invention are not covalently linked to functional groups comprising the amino acid side chains of the amino acids $A^1$, $A^2$, $A^3$ or $A^4$.

In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

It is an advantage of the somatostatin analogues provided by this invention that the thioether linkage is stable under the conditions of Tc-99m conjugation to the covalently linked Tc-99m binding moiety. In contrast, Tc-99m conjugation to a Tc-99m binding moiety covalently linked to native somatostatin, or to a somatostatin analogue having a disulfide bond, can result in reduction of the disulfide accompanied by a loss of biological activity. Such loss of biological activity can also occur in vivo using native somatostatin, or to any somatostatin analogue having a disulfide bond. The present invention is not subject to similar losses in biological activity in vivo because the thioether linkage in each of the somatostatin analogues of the invention is a stable covalent bond.

It is another advantage of the somatostatin analogues provided by this invention that the covalent linkage between the amino terminus and the cysteine protecting moiety acts to protect the peptide from degradation by exopepetidases.

In a preferred embodiment of the invention, a kit for preparing technetium-labeled peptides is provided. An appropriate amount of the peptide reagent is introduced into a vial containing a reducing agent, such as stannous chloride, in an amount sufficient to label the peptide with Tc-99m. An appropriate amount of a transfer ligand as described (such as tartrate, citrate, gluconate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form.

In a preferred embodiment, kit components are provided in lyophilized form.

Radiolabeled imaging reagents according to the present invention may be prepared by the addition of an appropriate amount of Tc-99m or Tc-99m complex into the vials and reaction under conditions described in Example 2 hereinbelow.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

The imaging reagents provided by the present invention can be used for visualizing organs such as the kidney for diagnosing disorders in these organs, and tumors, in particular gastrointestinal tumors, myelomas, small cell lung carcinoma and other APUDomas, endocrine tumors such as medullary thyroid carcinomas and pituitary tumors, brain tumors such as meningiomas and astrocytomas, and tumors of the prostate, breast, colon, and ovaries can also be imaged. In accordance with this invention, the Tc-99m labeled peptide reagents are administered in a single unit injectable dose. The Tc-99m labeled peptide reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The methods for making and labeling these compounds are more fully illustrated in the following Examples. These Examples illustrate certain aspects of the above-described method and advantageous results, and are shown by way of illustration and not limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluorophosphate/hydroxybenzotriazole (HBTU/HOBT), and using p-hydroxymethylphenoxymethyl-polystyrene (HMP) resin for carboxyl-terminus acids or Rink amide resin for carboxyl-terminus amides. Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature.

2-chloro- or 2-bromoacetyl groups were introduced either by using the appropriate 2-haloacetic acid as the last residue coupled during SPPS, or by treating the N-terminus free amino acid peptide bound to the resin with either 2-haloacetic acid/diisopropylcarbodiimide/N-hydroxysuccinimide/NMP or 2-haloacetic anhydride/diisopropylethylamine/NMP.

HPLC-purified 2-haloacetylated peptides were cyclized by stirring an 0.1–1.0 mg/mL solution in phosphate or bicarbonate buffer (pH 8.0) containing 0.5–1.0 mM EDTA for 4–48 h followed by acidification with acetic acid, lyophilization and HPLC purification. Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

The following somatostatin analogues were synthesized as provided herein, and the products of such synthesis identified by FABMS ($MH^+$ values in parentheses):

EXAMPLE 2

A General Method for Radiolabeling with Tc-99m 0.1 mg of a peptide prepared as in Example 2 was dissolved in 0.1 mL of water or 50 mM potassium phosphate buffer (pH=5, 6 or 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 $\mu$l of Tc-99m gluceptate was then added to the peptide and the reaction allowed to proceed at room temperature or at 100° C. for 15–30 min and then filtered through a 0.2 $\mu$m filter.

The Tc-99m labeled peptide purity was determined by HPLC using the following conditions:

1. The peptide is dissolved in 50 mM potassium phosphate buffer (pH 7.4) and labeled at room temperature.
2. The peptide is dissolved in 50 mM potassium phosphate buffer (pH 7.4) and labeled at 100° C.
3. The peptide is dissolved in water and labeled at room temperature.
4. The peptide is dissolved in water and labeled at 100° C.
5. The peptide is dissolved in 50 mM potassium phosphate buffer (pH 6.0) and labeled at 100° C.
6. The peptide is dissolved in 50 mM potassium phosphate buffer (pH 5.0) and labeled at room temperature.

General HPLC methods are as follows:

Solvents solvent A=0.1% $CF_3COOH/H_2O$ solvent $B_{70}$=0.1% $CF_3COOH/70\% CH_3CN/H_2O$ solvent $B_{90}$=0.1% $CF_3COOH/90\% CH_3CN/H_2O$ solvent flow rate=1 mL/min Columns Vydak 218TP54 RP-18, 5$\mu$×220 mm×4.6 mm analytical column with guard column Brownlee Spheri-5 RP-18, 5$\mu$×220 mm×4.6 mm column Methods 1. Brownlee column 100% A to 100% $B_{70}$ in 10 min
2. Vydak column 100% A to 100% $B_{90}$ in 10 min
3. Vydak column 100% A to 100% $B_{70}$ in 10 min Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

It should be understood that the foregoing disclosure emphasizes certain specific embodiments of the invention and that all modifications or alternatives equivalent thereto are within the spirit and scope of the invention as set forth in the appended claims.

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 1..5
        ( D ) OTHER INFORMATION: /label=Cyclized
            / note= "The peptide is cyclized between the sidechain sulfur of the cysteine residue and the amino terminus via an acetamido group; the trp ( x i ) SEQUENCE DESCRIPTION: SEQ ID NO:1:

Tyr  Trp  Lys  Thr  Cys
    1                   5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 1..5
        ( D ) OTHER INFORMATION: /label=Cyclized
            / note= "The peptide is cyclized between the
            sidechain sulfur of the cysteine residue and the
            amino terminus via an acetamido group; the trp ( x i ) SEQUENCE DESCRIPTION: SEQ ID NO:2:

Tyr  Trp  Lys  Thr  Cys  Thr
1                          5

What is claimed is:

1. A reagent for preparing a scintigraphic imaging agent comprising a peptide having a formula:

$$R^1(CR^2)-[C(R^3R^4)]_m-CO-(X^1)_nA^1A^2A^3A^4(X^2)_q NH-CH-X^3$$
$$\backslash S-(CR^7R^8)-(CR^5R^6)_p\backslash$$

wherein $R^1$ and $R^2$ are independently H, lower alkyl or substituted alkyl, aryl or substituted aryl;

$R^3$ and $R^4$ are each independently H, lower alkyl or substituted alkyl, aryl or substituted aryl, or either $R^3$ or $R^4$ are $N(R^{10})_2$, where each $R^{10}$ is independently H, lower alkyl or a peptide sequence of no more than 10 amino acids, and m is an integer between 0 and 3;

$X^1$ and $x^2$ are each independently a D- or L- amino acid, and n and q are independently either 0 or 1;

$A^1$ is D- or L-Phe or D- or L-Tyr or a substituted derivative thereof;

$A^2$ is D- or L-Trp or a substituted derivative thereof;

$A^3$ is D- or L-Lys or a substituted [derivatives] derivative thereof;

$A^4$ is Thr, Ser, Val, Phe, Ile or Aib;

$X^3$ is —COOR$^9$, —CH$_2$OH, CH$_2$COOR$^9$, or —CON$^9$)$_2$, where each $R^9$ is independently H, lower linear or cyclic alkyl or a substituted derivative thereof, or a peptide having an amino acid sequence of no more than 10 residues;

$R^5$ and $R^6$ are each independently H or lower alkyl and p is either 0, 1 or 2; and $R^7$ and $R^8$ are independently H, lower alkyl or substituted lower alkyl, or either $R^7$ or $R^8$ are —COOH or a derivative thereof;

wherein said peptide binds somatostatin receptor;

a carboxyl terminus of said peptide being covalently linked to a technetium-99m binding moiety selected from the group consisting of:

$$C(pgp)^s-(aa)-C(pgp)^s$$

wherein $C(pgp)^s$ is a cysteine having a protected thiol group and (aa) is any primary α or β-amino acid;

a technetium-99m binding moiety comprising a single-thiol moiety having a formula:

$$A-CZ(B)-[C(RR')]_n-X$$

wherein

A is H, HOOC, H$_2$NOC, or —NHOC;

B is SH or NHR";

X is H, methyl, SH or NHR";

Z is H or methyl;

R and R' are independently H or lower alkyl;

R" is H, lower alkyl or —C═O;

n is 0, 1 or 2; and where B is NHR", X is SH, Z is H and n is 1 or 2;

where X is NHR", B is SH, Z is H and n is 1 or 2;

here B is H, A is HOOC, H$_2$NOC, or —NHOC, X is SH, Z is H and n is 0 or 1;

where Z is methyl, X is methyl, A is HOOC, H$_2$NOC, or —NHOC, B is SH and n is 0;

and wherein the thiol moiety is in the reduced form;

$$\text{[phenyl]}-CO\text{-(amino acid)-cysteine-CO}-\overset{|}{SX} \quad [I.]$$

wherein

X=H or a protecting group;

(amino acid)=any amino acid;

$$-HN\text{-cysteine-(amino acid)-NH}-CH_2-\text{[pyridyl]}$$
$$\overset{|}{SX}$$

wherein

X=H or a protecting group;

(amino acid)=any amino acid;

$$\begin{array}{c} (CR_2)_n \\ NH \overset{}{\diagup} \quad \diagdown N-A-CO\text{-peptide} \\ | \qquad\qquad | \\ (CR_2)_m \qquad (CR_2)_p \\ | \qquad\qquad | \\ S\text{-}(pgp)^s \qquad S\text{-}(pgp)^s \end{array} \quad [III.]$$

wherein each R is independently H, CH$_3$ or C$_2$H$_5$;

each (pgp)$^s$ is independently a thiol protecting group or H;

m, n and p are independently 2 or 3;

A=linear or cyclic lower alkyl, aryl, heterocyclyl, a combination thereof or a substituted derivative thereof; and

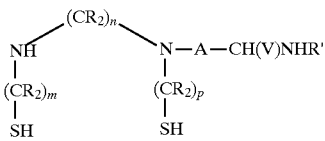 [IV.]

wherein each R is independently H, CH$_3$ or C$_2$H$_5$;

m, n and p are independently 2 or 3;

A=linear or cyclic lower alkyl, aryl, heterocyclyl, a combination thereof or a substituted derivative thereof, V=H or —CO-peptide;

R'=H or peptide;

and wherein when V=H, R'=peptide and when R'=H, V=—CO-peptide and wherein the technetium-99m binding moiety is capable of forming an electrically neutral complex with technetium-99m.

2. The reagent of claim 1 wherein the technetium-99m binding moiety is C(pgp)$^s$-(aa)-C(pgp)$^s$ and the thiol protecting group has a formula

wherein R is a lower alkyl having 1 to 6 carbon atoms, a 2-pyridyl, a 3-pyridyl, a 4-pyridyl, a phenyl, or a phenyl substituted with a lower alkyl, a hydroxy, a lower alkoxy, a carboxy, or a lower alkoxycarbonyl.

3. The reagent of claim 1 wherein the technetium-99m binding moiety has a formula:

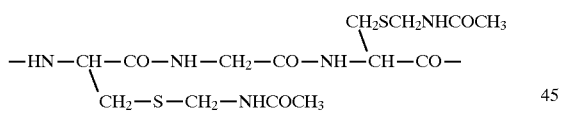

4. The reagent according to claim 1, wherein the peptide is chemically synthesized in vitro.

5. The reagent according to claim 4, wherein the peptide is synthesized by solid phase peptide synthesis.

6. The reagent according to claim 4, wherein the technetium-99m binding moiety is covalently linked to the peptide during in vitro chemical synthesis.

7. The reagent according to claim 6, wherein the technetium-99m binding moiety is covalently linked to the peptide during solid phase peptide synthesis.

8. A composition comprising a reagent comprising a somatostatin receptor-binding peptide selected from the group consisting of:

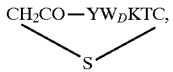

and

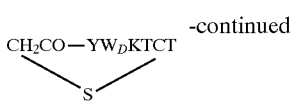
-continued said peptide being covalently linked to a technetium-99m binding moiety selected from the group consisting of:

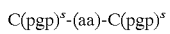

wherein C(pgp)$^s$ is a cysteine having a protected thiol group and (aa) is any primary α- or β- amino acid;

a technetium-99m binding moiety comprising a single-thiol moiety having a formula:

wherein

A is H, HOOC, H$_2$NOC, or —NHOC;

B is SH or NHR";

X is H, methl, SH or NHR";

Z is H or methyl;

R and R' are independently H or lower alkyl,

R" is H, lower alkyl or —C═O;

n is 0, 1 or 2;

and where B is NHR", X is SH, Z is H and n is 1 or 2;

where X is NHR", B is SH, Z is H and n is 1 or 2;

where B is H, A is HOOC, H$_2$NOC, or —NHOC, X is SH, Z is H and n is 0 or 1;

where Z is methyl, X is methyl, A is HOOC, H$_2$NOC, or —NHOC, B is SH and n is 0;

and wherein the thiol moiety is in the reduced form;

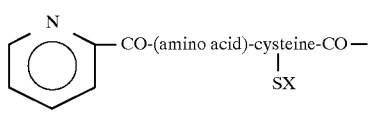

wherein

X=H or a protecting group;

(amino acid)=any amino acid;

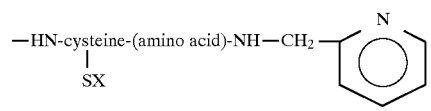

wherein

X=H or a protecting group;

(amino acid)=any amino acid;

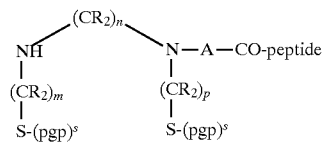

wherein each R is independently H, CH$_3$ or C$_2$H$_5$;

each (pgp)$^s$ is independently a thiol protecting group or H:

m, n and p are independently 2 or 3;

A=linear or cyclic lower alkyl, aryl, heterocyclyl, a combination thereof or a substituted derivative thereof; and

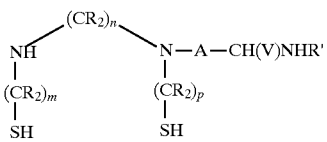

wherein
- each R is independently H, $CH_3$ or $C_2H_5$;
- m, n and p are independently 2 or 3;
- A=linear or cyclic lower alkyl, aryl, heterocyclyl, a combination thereof or a substituted derivative thereof;
- V=H or —CO-peptide;
- R'=H or peptide;
- and wherein when V=H, R'=peptide and when R'=H, V=—CO-peptide.

9. A reagent for preparing a radiolabled somatostatin receptor-binding agent comprising a peptide having a formula:

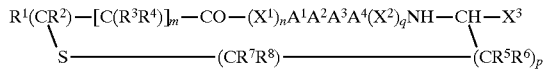

wherein
- $R^1$ and $R^2$ are independently H, lower alkyl or substituted alkyl, aryl or substituted aryl;
- $R^3$ and $R^4$ are each independently H, lower alkyl or substituted alkyl, aryl or substituted aryl, or either $R^3$ or $R^4$ are $N(R^{10})_2$, where each $R^{10}$ is independently H, lower alkyl or a peptide sequence of no more than 10 amino acids, and m is an integer between 0 and 3;
- $X^1$ and $X^2$ are each independently a D- or L- amino acid, and n and q are independently either 0 or 1;
- $A^1$ is D- or L-Phe or D- or L-Tyr or a substituted derivative thereof;
- $A^2$ is D- or L-Trp or a substituted derivative thereof;
- $A^3$ is D- or L-Lys or a substituted derivative thereof;
- $A^4$ is Thr, Ser, Val, Phe, Ile or Aib;
- $X^3$ is —$COOR^9$, —$CH_2OH$, $CH_2COOR^9$, or —$CON(R^9)_2$, where each $R^9$ is independently H, lower linear or cyclic alkyl or a substituted derivative thereof, or a peptide having an amino acid sequence of no more than 10 residues;
- $R^5$ and $R^6$ are each independently H or lower alkyl and p is either 0, 1 or 2; and
- $R^7$ and $R^8$ are independently H, lower alkyl or substituted lower alkyl, or either $R^7$ or $R^8$ are —COOH or a derivative thereof;

wherein said peptide binds somatostatin peptide;
and a radiolabel-binding moiety covalently linked thereto.

10. The reagent according to claim 9, wherein the peptide is chemically synthesized in vitro.

11. The reagent according to claim 10, wherein the radiolabel binding moiety is covalently linked to the peptide during solid phase peptide synthesis.

* * * * *